United States Patent [19]

Sinclair

[11] Patent Number: 5,216,050
[45] Date of Patent: Jun. 1, 1993

[54] BLENDS OF POLYACTIC ACID

[75] Inventor: Richard G. Sinclair, Columbus, Ohio

[73] Assignee: BioPak Technology, Ltd., Golden, Colo.

[21] Appl. No.: 579,000

[22] Filed: Sep. 6, 1990

Related U.S. Application Data

[63] Continuation-in-part of Ser. No. 387,676, Jul. 31, 1989, abandoned, which is a continuation-in-part of Ser. No. 229,894, Aug. 8, 1988, abandoned.

[51] Int. Cl.$^5$ .............. C08L 67/02; C08L 23/04; C08L 23/10; C08L 25/04
[52] U.S. Cl. .................. 524/108; 524/310; 524/317; 524/320; 525/186; 525/386; 525/411; 525/437
[58] Field of Search ............. 525/186, 411, 437, 386, 525/190, 415; 524/108, 310, 317, 320

[56] References Cited

U.S. PATENT DOCUMENTS

| | | | |
|---|---|---|---|
| 1,995,970 | 3/1935 | Dorough | 260/2 |
| 3,565,869 | 2/1971 | DeProspero | 260/78.3 |
| 3,636,956 | 1/1972 | Schneider | 128/335.5 |
| 3,755,558 | 8/1973 | Scribner | 424/47 |
| 3,982,543 | 9/1976 | Schmitt et al. | 128/335.5 |
| 4,279,249 | 7/1981 | Vert et al. | 128/92 D |
| 4,526,938 | 7/1985 | Churchill et al. | 525/415 |
| 4,534,349 | 8/1985 | Barrows | 128/334 R |
| 4,603,171 | 7/1986 | Hsieh | 525/105 |
| 4,621,638 | 11/1986 | Silvestrini | 128/335.5 |
| 4,646,741 | 3/1987 | Smith | 128/334 R |
| 4,661,530 | 4/1987 | Gogolewski et al. | 521/137 |
| 4,719,246 | 1/1988 | Murdoch et al. | 521/134 |
| 4,720,384 | 1/1988 | DiLuccio et al. | 424/78 |
| 4,741,337 | 3/1988 | Smith et al. | 128/334 R |
| 5,076,983 | 12/1991 | Loomis et al. | 264/101 |

FOREIGN PATENT DOCUMENTS

| | | |
|---|---|---|
| 58481 | 8/1982 | European Pat. Off. |
| 281482 | 9/1988 | European Pat. Off. |
| 311065 | 12/1989 | European Pat. Off. |
| 8400303 | 2/1984 | PCT Int'l Appl. |
| 8600533 | 1/1986 | PCT Int'l Appl. |
| 8700419 | 1/1987 | PCT Int'l Appl. |
| 9001521 | 2/1990 | PCT Int'l Appl. |

OTHER PUBLICATIONS

Biodegradable Materials of Poly(L–lactic acid): 1. Melt-spun and Solution-spun Fibres; Eling, B. et al; Polymer, vol. 23, Oct. 1982, pp. 1587-1593.

Porous Biomedical Materials Based on Mixtures of Polylactides and Polyurethanes; Gogolewski S., et al; Makromol. Chem. Rapid Commun., 3, 1982, pp. 839-845.

Microporous, compliant, biodegradable vascular grafts for the regeneration of the arterial wall in rat abdominal aorta; Van der Lei, B. et al; Surgery, 98, 1985, pp. 955-962.

Biodegradable PEO/PLA block copolymers; Cohn, Daniel et al; Journal of Biomedical Materials Research, vol. 22, pp. 993-1009 (1988).

Phase Separation in Poly(Ethylene Glycol)/Poly(Lactic Acid) Blends; Younes, H. et al; Eur. Polym. J. vol. 24, No. 8, 1988, pp. 765-773.

Survey of Polymer Blends Containing Poly(3–Hydroxybutyrate-co-16% Hydroxyvalerate); Dave, P. B. et al; Polymer Preprints, vol. 31, No. 1, Apr. 1990, pp. 442-443.

Novel Poly(d,l-Lactic Acid)—Ethylene/Vinyl Acetate Blends for Controlled Release Applications; Dollinger, H. M. et al; Polymer Preprints, vol. 31, No. 1, Apr. 1990, pp. 429-430.

Primary Examiner—Patricia A. Short
Attorney, Agent, or Firm—Sheridan, Ross & McIntosh

[57] ABSTRACT

An environmentally degradable composition comprising blends of a physical mixture of poly(lactic acid), and a polymer selected from the group consisting of poly(ethylene terephthalate), a polymer or copolymer of styrene, ethylene, propylene, vinyl chloride, vinyl acetate, alkyl methacrylate, alkyl acrylate, and physical mixtures thereof; plasticized with D-lactic acid, L-lactic acid, racemic D,L-lactic acid, D-lactide, L-lactide, meso D,L-lactide, racemic, D,L-lactide, oligomers of lactic acid, oligomers of lactide, derivatives of oligomers of lactic acid, or various mixtures thereof.

13 Claims, 1 Drawing Sheet

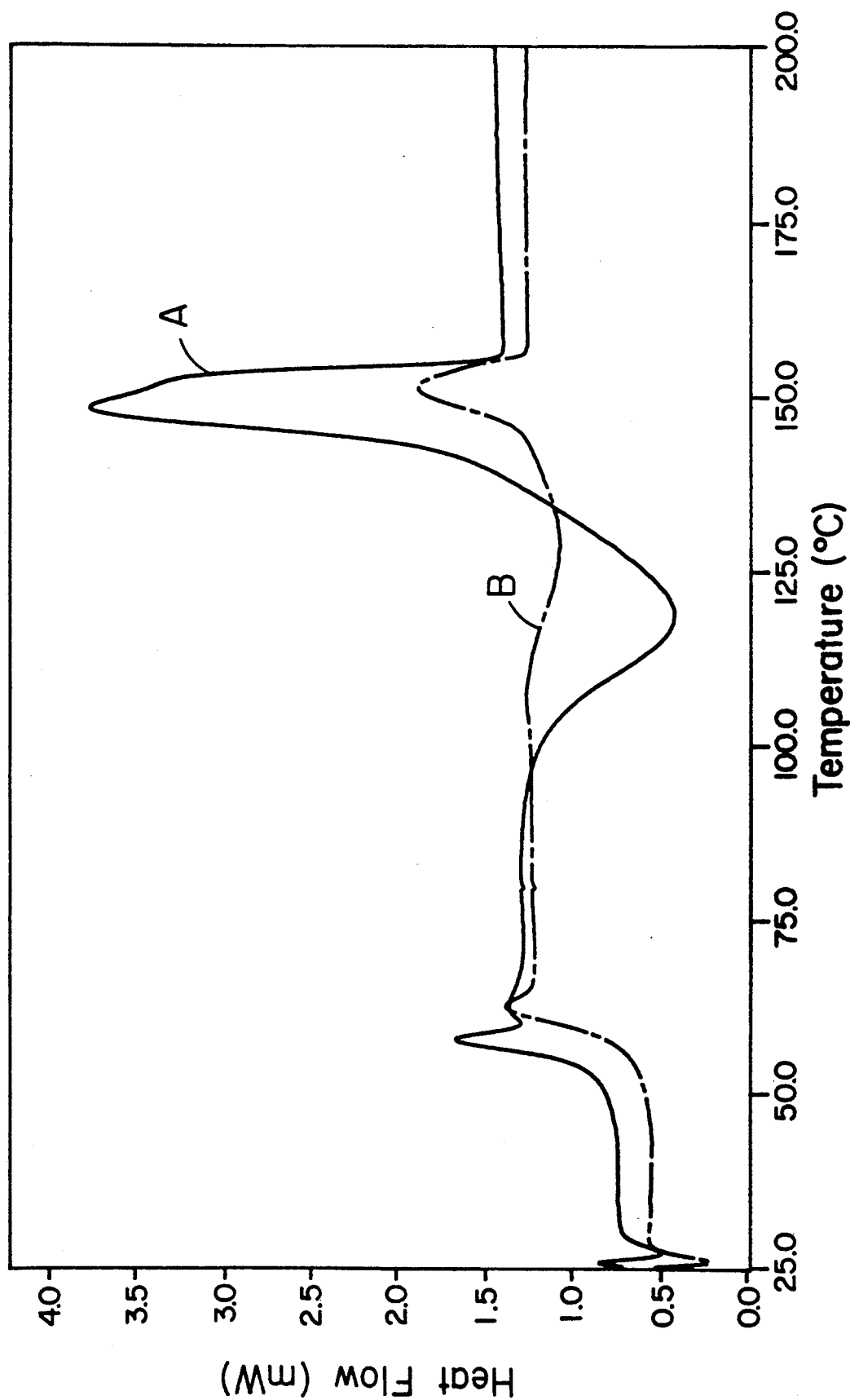

BLENDS OF POLYACTIC ACID

This is a continuation-in-part of copending application Ser. No. 07/387,676 filed on Jul. 31, 1989 now abandoned; which is a continuation-in-part of Ser. No. 07/229,894 filed on Aug. 8, 1988, now abandoned.

FIELD OF THE INVENTION

The invention relates to the blending of conventional thermoplastics with poly(lactic acid). This provides novel, environmentally degradable thermoplastics. The environmentally degradable thermoplastics are useful in a wide variety of applications.

The invention further relates to a method for producing pliable films and other packaging items and to the unique product thereof. The invention has utility in producing a product that has the characteristics of the usual plastics yet is environmentally degradable.

The present application is related to the application entitled BIODEGRADABLE PACKAGING THERMOPLASTICS FROM POLY(LACTIC ACID) having Ser. No. 07/579,005, the application entitled BIODEGRADABLE REPLACEMENT OF CRYSTAL POLYSTYRENE having Ser. No. 07/579,465, and the application entitled DEGRADABLE IMPACT MODIFIED POLY(LACTIC ACID) having Ser. No. 07/579,460, all having the same assignee and filing date as the present application, the disclosures of which are incorporated by reference herein.

BACKGROUND OF THE INVENTION

There is a need for an environmentally degradable packaging thermoplastic as an answer to the tremendous amounts of discarded plastic packaging materials. U.S. plastic sales in 1987 were 53.7 billion lbs of which 12.7 billion lbs were listed as plastics in packaging. A significant amount of this plastic is discarded and becomes a plastic pollution that is a blot on the landscape and a threat to marine life.

A further problem with the disposal of plastic packaging is the concern for dwindling landfill space. It has been estimated that most major cities will have used up available landfills for solid waste disposal by the early 1990's. Plastics comprise approximately 3 percent by weight and 6 percent of the volume of solid waste.

One other disadvantage of conventional plastics is that they are ultimately derived from petroleum, which leaves plastics dependent on the uncertainties of foreign crude oil imports. A better feedstock would be one that partially derives from renewable, domestic resources thus reducing reliance on imports.

However, there are good reasons for the use of packaging plastics. They provide appealing aesthetic qualities in the form of attractive packages which can be quickly fabricated and filled with specified units of products. The packages maintain cleanliness, storage stability, and other desirable qualities such as transparency for inspection of contents. These packages are known for their low cost of production and chemical stability. This stability, however leads to very long-life of the plastic, so that when its one-time use is completed, discarded packages remain on, and in, the environment for incalculably long times.

There are many citations in the prior art for the preparation of lactic acid polymers and copolymers. The earliest processes used lactic acid directly as the monomer, cf., eg., U.S. Pat. Nos. 1,995,970; 2,362,511; and 2,683,136. The poly(lactic acids) of these patents were of low molecular weights, tacky and without good physical properties. U.S. Pat. No. 2,668,162 (Lowe, DuPont) discloses the use of lactide as the monomer. Lactide is the dilactone of lactic acid and is an internal ester of lactic acid. When lactide is formed, byproduct water is eliminated, permitting the lactide subsequently to be ring-opened polymerized to linear polyester of high molecular weight without tedious condensation methods. Polymers and copolymers of excellent physical properties were obtained by using the intermediate, lactide, to form poly(lactic acid). Copolymers of lactide and glycolide are disclosed by the Lowe patent which are tough, clear, cold-drawable, stretchable, and capable of forming at 210 C into self-supporting films.

Other patents related to forming lactide polymers include U.S. Pat. Nos. 2,703,316; 2,758,987; 2,951,828; 3,297,033; 3,463,158; 3,531,561; 3,636,956; 3,736,646; 3,739,773; 3,773,929; 3,887,699; 3,797,499; 4,273,920; 4,471,077; and 4,578,384; German Offenlegungsschrift 2,118,127; Canadian Patents 808,731; 863,673; and 923,245. U.S. Pat. No. 3,636,956 teaches an interweaving of fibers that is not blending or melt blending of a composition to make a physical mixture.

U.S. Pat. No. 4,719,246 teaches the blending of homopolymers of L-lactide, D-lactide, polymers of mixtures thereof; and copolymers of L-lactide or D-lactide with at least one nonlactide comonomer. The blending is intended to produce compositions having interacting segments of poly(L-lactide) and poly(D-lactide).

U.S. Pat. No. 4,661,530, discloses the mixtures of a poly(L-lactic acid) and/or poly (D,L-lactic acid) and segmented polyester urethanes or polyether urethanes. Biodegradable materials are formed that are useful in synthetic replacements of biological tissues and organs in reconstructive surgery.

PCT publication W0 87/00419 to Barrows reveals a bone spacer comprising a blend or mixture of a nonabsorbable polymer and a bioabsorbable polymer, poly(-lactic acid) is one of the preferred biodegradable polymers but plasticizers are not revealed thererin. PCT publication W0 84/00303 to Gogolewski et al suggests blends of polyesters and polyurethanes for preparing surgical filaments.

BRIEF DESCRIPTION OF THE INVENTION

An environmentally degradable composition comprising blends of a physical mixture of poly(lactic acid); one or more polymers selected from the group consisting of a poly(ethylene terephthalate), a polymer or copolymer of styrene, ethylene, propylene, vinyl chloride, vinyl acetate, alkyl methacrylate, alkyl acrylate, and physical mixtures thereof; and one or more plasticizers discussed below.

The poly(lactic acid) present in the blends may be represented by the structure:

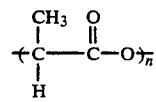

where n is an integer between 75 and 10,000.

Plasticizers useful with the invention include D-lactic acid, L-lactic acid, racemic D,L-lactic acid, D-lactide, L-lactide, meso D,L-lactide, racemic D,L-lactide, oligomers of lactic acid, oligomers of lactide, and mixtures thereof. The oligomers of lactic acid, and oligomers of lactide are defined by the formula:

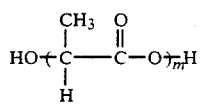
  II where ms is an integer: $2 \leq m \leq 75$. Preferably m is an integer: $2 \leq m \leq 10$. These limits correspond to number average molecular weights below about 5,400 and below about 720 respectively.

Further plasticizers useful in the invention include derivatives of oligomeric lactic acid, selected from the group defined by the formula:

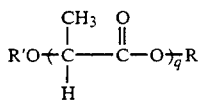
  III where R=H, alkyl, aryl, alkylaryl or acetyl, and R is saturated, where R'=H, alkyl, aryl, alkylaryl or acetyl, and R' is saturated, where R and R' cannot both be H, where q is an integer: $2 \leq q \leq 75$; and mixtures thereof. Preferably q is an integer; $2 \leq q \leq 10$. As used herein the term "derivatives of oligomeric lactic acid" includes derivatives of oligomeric lactide.

The plasticizers may be present in any amount that provides the desired characteristics. For example, the various types of plasticizers discussed herein and in the copending applications provide for (a) more effective compatibilization of the melt blend components; (b) improved processing characteristics during the blending and processing steps; and (c) control and regulate the sensitivity and degradation of the polymer by moisture. For pliability, plasticizer is present in higher amounts while other characteristics are enhanced by lower amounts. The compositions allow many of the desirable characteristics of pure nondegradable polymers. In addition, the presence of plasticizer facilitates melt processing, prevents discoloration, and enhances the degradation rate of the compositions in contact with the environment. The intimately plasticized composition should be processed into a final product in a manner adapted to retain the plasticizer as an intimate dispersion in the polymer for certain properties. These can include: (1) quenching the composition at a rate adapted to retain the plasticizer as an intimate dispersion; (2) melt processing and quenching the composition at a rate adapted to retain the plasticizer as an intimate dispersion; and (3) processing the composition into a final product in a manner adapted to maintain the plasticizer as an intimate dispersion. The plasticizers are preferably at least intimately dispersed within the poly(lactic acid) if not in the coblended polymer.

Particularly advantageous is the sequential incorporation of plasticizer into poly(lactic acid) and the other polymer by melt blending with them, a first plasticizer selected from the group consisting of oligomers of lactic acid, oligomers of lactide, and mixtures thereof; and melt blending with the blend a second plasticizer selected from the group consisting of lactic acid, L-lactide, D-lactide, meso D,L-lactide, racemic D,L-lactide, and mixtures thereof. If desired, a first plasticizer defined by the formula III may be used along or in admixture with an oligomer of formula II. This procedure allows the blending of the first plasticizer at a first temperature and the blending of the second plasticizer at a second temperature lower than the first temperature.

BRIEF DESCRIPTION OF THE DRAWING

The FIGURE illustrates a differential scanning calorimetry (DSC) of 90/10, L-/D,L-lactide copolymer blended with 5 weight percent polystyrene.

DETAILED DESCRIPTION OF THE INVENTION AND PREFERRED EMBODIMENTS

The present invention discloses the blending of poly(lactic acid) (PLA) with polystyrene (PS), polyethylene (PE), polyethylene terephthalate (PET), and polypropylene (PP). The invention discloses that poly(lactic acid) is melt compatible with these conventional thermoplastics and the effect on their physical properties. Since both lactic acid and lactide can achieve the same repeating unit, the general term poly(lactic acid) as used herein refers to polymers having the repeating unit of formula I without any limitation as to how the polymer was made (e.g. from lactides, lactic acid, or oligomers), and without reference to the degree of polymerization or level of plasticization.

The environmentally degradable compositions disclosed herein are at least partially degradable. That is the poly(lactic acid) portion of the composition will decompose relatively rapidly compared to the more stable portions of the blend and cause a physical deterioration of the blended material. For example, when the compositions are intimate and homogeneous blends with small domain sizes the physical deterioration will destroy the original formed product. The compositions herein provide environmentally acceptable materials because their physical deterioration and degradation is much more rapid than conventional nondegradable plastics. Further, since a significant portion of the composition can be poly(lactic acid), and/or a lactic acid derived lactide or oligomer only a small portion of more slowly degrading thermoplastic residue will remain (e.g. polystyrene). This residue will have a high surface area and is expected to decompose faster than a bulk formed product.

D-lactide is a dilactone, or cyclic dimer, of D-lactic acid. Similarly, L-lactide is a cyclic dimer of L-lactic acid. Meso D,L-lactide is a cyclic dimer of D-, and L-lactic acid. Racemic D,L-lactide comprises a 50/50 mixture of D-, and L-lactide. When used alone herein, the term "D,L-lactide" is intended to include meso D,L-lactide or racemic D,L-lactide. Poly (lactic acid) may be prepared from one or more of the above.

EXAMPLE 1

Polystyrene was solvent blended with poly(lactic acid) and solvent cast from $CH_2Cl_2$ to determine optimum compatibility. The solvent cast films were translucent and apparently "noncheesy". A sample, appears homogeneous to the naked eye and resists folding and handling without shredding apart. Optical microscopy at 310X reveals heterogeneous domains of 3 microns and less. The blend is apparently very compatible. It exhibits no change over 2 years with regard to "blooming" of fugitive material nor does its physical properties show evidence of degradation.

EXAMPLE 2

Polypropylene 8525, Hercules, was similarly melt blended in the Brabender with poly(lactic acid) at 400 F. Ratios of PP/PLA prepared were 100/0 for the control, 90/10, and 75/25.

EXAMPLES 3-5

Melt blends were prepared of poly(lactic acid) with polystyrene. Both a high molecular weight polystyrene (Piccolastic, E-125, Hercules) and a low molecular weight polystyrene (Piccolastic, D-100) were investigated. Also used was a general purpose polystyrene, (Huntsman polystyrene 208), a crystal polystyrene. These were mixed in a Brabender at 325 F at different ratios with poly(lactic acid).

The polystyrene/poly(lactic acid) ratios used were 100/0 for the control, and 90/10, and 75/25 for the Huntsman 208, general purpose polystyrene.

EXAMPLES 6-7

Two types of polyethylene terephthalate were used. (Goodyear's "Clearstuff" and Eastman's Kodapak TN-0148). These were dried overnight at 90 C and melt blended at 525 F in a Brabender with poly(lactic acid) for only a few minutes. The poly(lactic acid) reduced the melt viscosity.

EXAMPLES 8-16

The controls and blends for polypropylene, general purpose polystyrene, and polyethylene terephthalate (Eastman's) from Examples 2-7 were ground in a Abbey grinder and compression molded into approximately 5 mil films. Polypropylene-poly(lactic acid) films were molded at about 400 F; polystyrene-poly(lactic acid) films were obtained at 250-300 F; polyethylene terephthalate-poly(lactic acid) films were molded at about 525 F. After conditioning at 50 percent r.h. and 23 C for 24 hours they were tested on the Instron. The controls were similarly treated. Samples of the compression molded film were placed in an Atlas Weather-O-Meter for weatherability evaluation (cycles of 102 minutes of sunshine and 18 minutes of rain). The results of these Examples are shown in Table I.

EXAMPLES 17-19

Three samples of 100 percent poly(lactic acid) using poly(D,L-lactic acid) were prepared as above but with film thicknesses of 10-15 mil. Tests were performed as in Examples 20-27 below except that the second sample was tested after 82 hours of exposure to 50 percent relative humidity at 72 F.

EXAMPLES 20-27

High density polyethylene, HDPE, (0.960 g/cc) was melt blended with poly(lactic acid) in the Brabender Plasticorder at 151 C for 10 minutes. Blend ratios of high-density polyethylene/poly(lactic acid) of 100/0 for the controls, 90/10, 80/20 and 50/50 were used. Two samples of each were prepared. The blends were ground in an Abbey grinder and compression molded into 10-15 mil films. The films were tested in an Atlas Weather-O-Meter set for 51 minutes of carbon arc light and 9 minutes of water spray. Temperature was varied from ambient to 140 F. Tensile strengths, elongation to yield tests and classification of the tensile failure were performed for the samples as shown in Table 2.

EXAMPLES 28-33

Low density polyethylene, LDPE, (0.917 g/cc) was melt blended with poly(lactic acid) in the Brabender Plasticorder at 151 C for 10 minutes. Blend ratios of low density polyethylene/poly(lactic acid) of 100/0 for the controls 90/10 and 50/50 were used. Two samples of each were prepared. The samples were treated and evaluated as in the case of Examples 20-27. Results are shown in Table 2.

EXAMPLES 34

In a 500-ml, 3-neck, round bottom flask, equipped with a mechanical stirrer and a nitrogen inlet and outlet, was placed 180.7 g of L-lactide and 40.2 g of racemic D,L-lactide (both Boehringer and Ingelheim, grade S). The contents of the flask were heated to 110 C under a nitrogen sweep to melt the lactides and 20.1 g of polystyrene (Amoco R3, melt index 3.5 g/10 min.) was added. The polystyrene swelled highly and partially dissolved while stirring overnight and advancing the heat to 185 C. The temperature was decreased to 141 C and 0.2 ml of anhydrous stannous octoate solution (0.2 ml/ml of toluene) was added. The stirrer was turned off and the lactides allowed to polymerize at 141 C over 3 days time. The highly swollen, polystyrene floated to the top after turning off the stirrer. The lower, polylactide phase was cooled and examined by differential scanning calorimetry (DSC). The sample has a low Tg, approximately 35 C, and is otherwise lacking in apparent temperature transitions. Compression-molded films are clear, colorless, and very pliable. These results indicate that the polystyrene thoroughly interrupts crystallinity formation under these conditions.

EXAMPLE 35

Poly(lactic acid) was mill roll blended with crystal polystyrene. The blend revealed excellent compatibility of polystyrene dispersed in poly(lactic acid). Thus 5 weight percent of polystyrene was dispersed in a 90/10 ratio of L-/racemic, D,L-lactide copolymer in a two roll mill at 170 C. The material became hazy and exhibited considerable crystallinity by thermal analysis. This example demonstrates that under these conditions polystyrene easily induces crystallinity in poly(lactic acid). A thermal analysis of the material, see the Drawing, reveals that the material remains crystalline even when heated and cooled.

The Examples 34 and 35 illustrate that poly(lactic acid) blended with the environmentally nondegradable plastics herein can produce final properties in the mixture depending on the mixing or blending technique used.

DISCUSSION

Brabender melt-blends of all types exhibited small heterogeneous particle sizes of 10 microns or less. The tensile strengths were evaluated before, and after, simulated weathering. After 1248 hours (52 days) in the Atlas Weather-O-Meter all of the polypropylene samples were whitened, extremely brittle and were not able to be tested. The polypropylene samples were retested at shorter intervals as shown in Table 1. At approximately 300 hours of weathering in the Atlas Weather-O-Meter, the samples exhibited significant environmental degradation.

The polystyrene blends with poly(lactic acid) exhibited environmental degradation that was apparent after 300 hours of simulated weathering. The polyethylene terephthalate blends were also visibly environmentally degraded in approximately 300 hours.

TABLE 1
TENSILE STRENGTH OF FILMS BEFORE, AND AFTER ACCELERATED WEATHERING[a]

| Blend Ratio and Material | Tensile Strength[b]/% Elongation | | |
|---|---|---|---|
| | Before | After, 310 hours | After, 400 hours |
| 100/0 PP[c]/PLA | 1665/61 | 585.1.6 | 494/1.7 |
| 90/10, PP/PLA | 1568/51 | 954/3.2 | 346/— |
| 75/25, PP/PLA | 1124/14 | 370/1.1 | 254/1.0 |
| 100/0 PS[d]/PLA | 3200/2.0 | 1066/1.0 | — |
| 90/10, PS/PLA | 2350/2.0 | 582/1.0 | — |
| 75/25, PS/PLA | 1493/1.6 | 484/1.0 | — |
| 100/0 PET[e]/PLA | 3036/— | 3509/3.0 | — |
| 90/10, PET/PLA | 2147/— | 1378/3.0 | — |
| 75/25, PET/PLA | 2743/— | 2041/3.0 | — |

[a]Weather-o-meter, cycle of 102 minutes of sunshine, 18 minutes of rain.
[b]0.05 in./min., on the Instron.
[c]Hercules polypropylene 825.
[d]Huntsman 208.
[e]Tennessee Eastman, Kodapak TN 0148.

The poly(lactic acid), high density polyethylene, low density polyethylene, and their blends were evaluated for physical strength, before, and after simulated weathering and the results are shown in Table 2.

TABLE 2
PHYSICAL PROPERTIES OF POLYETHYLENE (PE), POLYLACTIC ACID (PLA), AND THEIR BLENDS, BEFORE, AND AFTER, WEATHER-O-METER EXPOSURES

| Material[a] | Material Blend Ratio[b] Polymer/PLA | Weather-O-Meter[c] Exposure, hours | Tensile Strength, psi | Elongation[d] to Yield, % | Type of Tensile Failure |
|---|---|---|---|---|---|
| 100% PLA[e] | 0/100 | 0 | 6,030 | 2.2 | Brittle |
| 100% PLA | 0/100 | 0[f] | 5,670 | 2.1 | Brittle |
| 100% PLA | 0/100 | 82 | (too brittle to test) | — | Brittle |
| 100% HDPE[g] | 100/0 | 0 | 3,540 | 8 | Ductile |
| 100% HDPE | 100/0 | 233 | 1,400 | 1 | Brittle |
| HDPE/PLA | 90/10 | 0 | 3,480 | 7 | Ductile |
| HDPE/PLA | 90/10 | 233 | 1,720 | 1 | Brittle |
| HDPE/PLA | 80/20 | 0 | 3,180 | 4 | Brittle |
| HDPE/PLA | 80/20 | 125 | 2,150 | 2 | Brittle |
| HDPE/PLA | 50/50 | 0 | 2,720 | 2 | Brittle |
| HDPE/PLA | 50/50 | 233 | (too brittle to test) | — | Brittle |
| 100% LDPE[h] | 100/0 | 0 | 1,320 | 80 | Ductile |
| 100% LDPE | 100/0 | 125 | 1,250 | 67 | Ductile |
| LDPE/PLA | 90/10 | 0 | 1,190 | 31 | Ductile |
| LDPE/PLA | 90/10 | 125 | 855 | 14 | Ductile |
| LDPE/PLA | 50/50 | 0 | 1,160 | 4 | Ductile |
| LDPE/PLA | 50/50 | 125 | (too brittle to test) | — | Brittle |

[a]Compression-molded films, 10-15 mil thickness.
[b]Melt-blended in Brabender Plasticorder for 10 minutes, 151 C.
[c]51 minutes of carbon arc light and 9 minutes of water spray for each 1 hour cycle. Temperature varies from ambient to 140 F.
[d]Elongation at maximum in strain curve.
[e]Poly(D,L-lactic acid), $\{\eta\} = 1.16$ dl/g, 25 C., THF.
[f]After 82 hours exposure to 50% R.H., 72 F.
[g]High density polyethylene, density 0.960 g/cc, melt index 0.6 g/10 minutes.
[h]Low density polyethylene, density 0.917 g/cc, melt index 0.25 g/10 minutes.

The poly(lactic acid) and its blends were much more environmentally degradable than the pure low density or high density polyethylene. The high density polyethylene samples degraded substantially without weight loss while the high density polyethylene-poly(lactic acid) blends exhibited weight loss, particularly where microscopy revealed poly(lactic acid) was exposed at the surface of the films. The high density polyethylene degraded by exposure to actinic light as shown by microscopy.

With all of the samples, increasing the percentage of poly(lactic acid) decreased the tensile strength before, and after, simulated weathering. The incorporation of poly(lactic acid) introduced a faster degradation in blends of polypropylene, polystyrene, polyethylene terephthalate, and high and low density polyethylene. Presumably, the actinic light as well as hydrolysis of the polyesters degrades the polymer. The small size of the spherical, microheterogeneous, domains of the blend are undoubtedly poly(lactic acid), which is mostly buried. Therefore, poly(lactic acid) hydrolysis is slow. Faster degradation via hydrolysis can be achieved by controlling the location of the poly(lactic acid). This, in turn, is related to the rheology of the blend during melt blending. The small size of the dispersed, heterogeneous domains indicates good compatibility of the mixed polymers.

In a simulated landfill, where light is excluded, the controls and the blends show much slower rates of degradation. With hydrolysis, alone, the poly(lactic acid) samples slowly whiten, while the blends are qualitatively unchanged for the time period tested.

Conversely, addition of minor amounts of nondegradable thermoplastics to poly(lactic acid) to form compatible blends, using, for example, polypropylene, polystyrene, polyethylene terephthalate and high and low density polyethylene will retard the degradation rate of the poly(lactic acid). A preferred compositional range is from 80-99 weight percent poly(lactic acid).

A general description of the environmentally degradable composition comprises blends of a physical mixture of poly(lactic acid) (polylactide), and a polymer selected from the group consisting of a poly(ethylene terephthalate), a polymer or copolymer of styrene, ethylene, propylene, vinyl chloride, vinyl acetate, alkyl methacrylate, alkyl acrylate, and physical mixtures thereof. Other possible compositional blends are listed below in the discussion of process embodiments of the invention. While the level of plasticizer can vary over wide ranges depending on the amount of poly(lactic acid) present and the type of coblended polymer, the preferred amount for a stiff material is generally about 0.1 to about 10 weight per cent.

The blends preferably use a physical mixture of poly(lactic acid) of the structure:

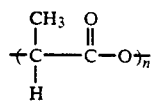   I where n is an integer between 75 and 10,000; and a polymer selected from the group consisting of polystyrene, polyethylene, poly(ethylene terephthalate), and polypropylene and other compositions further discussed below. The composition of poly(lactic acid) in the composition may vary over wide limits such as about 1/99 to about 99/1. A preferred composition is that where the poly(lactic acid) comprises 5 to 50 weight percent of the composition. Another preferred composition has a poly(lactic acid) content of about 10 to 20 weight percent, and another about 80 to 99. The ratio will depend on desired characteristics.

The polymers and copolymers selected from the group above, deemed the added polymer, can be used alone or in combination. The group is not restricted to those cited above since other polymer types are noted as compatible with poly(lactic acid). These include the polymers and copolymers comprised from the group of ethylene, proplyene, styrene, vinyl chloride, vinyl acetate, alkyl methacrylates, and alkyl acrylates. It should be understood that the term copolymers as used herein includes polymers made from mixtures of the monomers in the listed group. Physical mixtures of the polymers and copolymers of the above group are likewise useful in the invention.

A first embodiment of the process for producing the composition includes providing a poly(lactic acid); selecting a polymer from the group consisting of a poly(ethylene terephthalate), a polymer or copolymer of styrene, ethylene, propylene, vinyl chloride, vinyl acetate, alkyl methacrylate, alkyl acrylate, and physical mixtures thereof; and blending the polymers. The blending may be by melt blending on a mill roll or by compounding in an extruder or by other mechanical means. The poly(lactic acid) provided preferably has the formula I and contains plasticizers as discussed herein.

A second embodiment of the process for producing the composition of the invention includes providing a lactide selected from the group consisting of D-lactide, L-lactide, meso D,L-lactide, racemic D,L-lactide, and mixtures thereof; selecting a polymer from the group consisting of the polymers or copolymers of styrene, ethylene, ethylene terephthalate, propylene, vinyl chloride, vinyl acetate, alkyl methacrylate, alkyl acrylate, and physical mixtures thereof. The selected lactide and polymer are mixed and heated to melt the lactide and at least partially dissolve the polymer. Finally, the lactide, is at least partially polymerized to obtain a blend of polylactide, unpolymerized lactide monomer and the selected polymer. The polymerization is preferably controlled by monitoring the amount of lactide remaining and stopping the polymerization at the desired level. If desired, the polymerization can be carried to completion. Additional lactide monomer or other plasticizers such as lactic acid, oligomers of lactic acid, oligomers of lactide, and mixtures thereof, where the oligomers are defined by the formula:

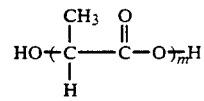   II where m is an integer: $2 \leq m \leq 75$, where the oligomers preferably have a number average molecular weight below about 5,400 and most preferably below about 720; as well as one or more derivatives of an oligomer of lactic acid defined by the formula:

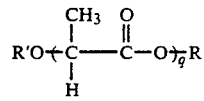   III where $R = H$, alkyl aryl, alkylaryl or acetyl, and R is saturated, where $R' = H$, alkyl aryl, alkylaryl or acetyl, and R' is saturated, where R and R' cannot both be H, and where q is an integer: $2 \leq q \leq 75$, ca be added to obtain desired characteristics as taught in the U.S. copending applications having the titles "BIODEGRADABLE PACKAGING THERMOPLASTICS FROM POLY(LACTIC ACID)" and "BIODEGRADABLE REPLACEMENT OF CRYSTAL POLYSTYRENE". Additionally, the various types of plasticizers discussed herein and in the copending applications provide for (a) more effective compatibilization of the melt blend components; (b) improved processing characteristics during the blending and processing steps; and (c) control and regulate the sensitivity and degradation of the polymer by moisture.

It will be obvious to those skilled in the art that the proportions of poly(lactic acid) and the added polymer can vary widely depending on their mutual solubilities. Solubilities, in turn, vary with the thoroughness of mixing and the mixing temperature. While placing both the poly(lactic acid) and the added polymer into a mutual solvent solution will obtain intimacy, the use of solvent is impractical for many commercial processes. Physical mixing, such as melt blending on a mill-roll or extruder is more practical, but must be controlled to achieve an intimate dispersion, that is, high shear is required to achieve the desired intimacy. Even with intimate mixing different polymers may not be compatible, that is, they may still separate into relatively large heterogeneous domains of, for example, 10 to 100 micron size, or larger. This results in a "cheesy" mixture, or a blend with poor properties. What is surprising is that poly(lactic acid) is easily blend compatible with a wide variety of other polymers, including both polar and nonpolar polymers.

The temperature of the melt blending of the poly(lactic acid) with other polymers may be varied to adjust the proportions of the poly(lactic acid) with one, or more, added polymers. At lower temperatures, the solubilities may not be adequate, while too high a temperature will cause decomposition of the mixture. A general temperature range is 100–220 C, and the preferred range is 130–180 C. Equally significant are the melt viscosities of the different polymer components. With increasing molecular weight, the viscosities increase sharply. By controlling the proportions of the poly(lactic acid) and the added polymer, or polymers, the temperature, the mixing type and time, and the molecular weight, a wide range of mixtures can be obtained. Thus, for example, the poly(lactic acid) can be dispersed into the added polymer, or polymers, or vice versa, and the size and geometry of the dispersed phase varied greatly, ranging from discrete spheres to strands of different diameters or lengths. This results in a wide latitude of physical properties and degradation times in the environment. The weight percent ratio of poly(lactic acid) to the selected polymer can be between 99:1 to 1:99.

Where the lactide monomer is used to dissolve the added polymer and the lactide is subsequently polymerized, the temperature of mixing and polymerizing must be balanced between the mutual solubilities and the reactivity of the lactide. Higher temperatures generally produce lower molecular weight poly(lactic acid). A further embodiment of the invention is to mix at one temperature and polymerize at another temperature to achieve variations in the geometry of the dispersed phase, as discussed above.

The compositions herein can be processed by melt fabrication into useful articles of manufacture having a self supporting structure such as disposable containers, eating utensils, trays, plates, drinking cups, single serving trays, syringes, medical trays, packaging films and the like. The compositions are useful in that they can have the characteristics of the usual plastics and therefore substitute for them yet degrade in the environment. The compositions are especially useful for articles having only a one time use or a short life span in use before disposal.

While the invention has been described above with reference to various specific examples and embodiments, it will be understood that the invention is not limited to such illustrated examples and embodiments and may be variously practiced within the scope of the claims hereinafter made.

I claim:

1. A process for producing an environmentally degradable composition comprising:
   a. providing lactide monomer selected from the group consisting of D-lactide, L-lactide, meso D,L-lactide, racemic D,L-lactide and mixtures thereof;
   b. selecting a first polymer from the group consisting of poly(ethylene terephthalate), a polymer or copolymer of styrene, ethylene, propylene, vinyl chloride, vinyl acetate, alkyl methacrylate, alkyl acrylate, and physical mixtures thereof;
   c. mixing and heating the lactide selected in (a) and the polymer selected in (b) at conditions adapted to melt the lactide and at least partially dissolve the polymer; and
   d. polymerizing the lactide in the mixture of step (c) to obtain a blend of a physical mixture comprising polylactide and the first polymer as heterogeneous phases.

2. The process of claim 1 comprising the step:
   e. forming the blend into a self supporting structure.

3. The process of claim 1, wherein the polymerization of step (d) is controlled to obtain a blend containing residual monomer.

4. The process of claim 1, comprising:
   e. adding to the blend after polymerization a plasticizer selected from the group consisting of lactic acid, D-lactide, L-lactide, meso D,L-lactide, racemic D,L-lactide, oligomers of lactic acid, oligomers of lactide, and mixtures thereof, wherein oligomers have a number average molecular weight below about 5,400.

5. The process of claim 4, comprising adding a plasticizer in an amount effective to provide compatibilization of the melt blend components.

6. The process of claim 4, comprising adding a plasticizer in an amount effective to regulate the compositions' sensitivity to degradation by moisture.

7. The process of claim 4, comprising providing a plasticizer selected from the group consisting of an oligomer of lactide, or an oligomer of lactic acid having a number average molecular weight below about 720.

8. The process of claim 4, comprising: providing a plasticizer selected from the group consisting of one or more derivatives of an oligomer of lactic acid and an oligomer of lactide defined by the formula:

$$R'O\!\!-\!\!\left(\!\!\begin{array}{c}CH_3\\|\\C\\|\\H\end{array}\!\!-\!\!\begin{array}{c}O\\\|\\C\end{array}\!\!-\!\!O\right)_{\!\!q}\!\!R$$

where R=H, alkyl, aryl, alkylaryl or acetyl, and R is saturated, were R'=H, alkyl, aryl, alkylaryl or acetyl, and R' is saturated where R and R' cannot both be H, and where q is an integer: $2 \leq q \leq 75$.

9. The process of claim 4, comprising:
   a. providing a first plasticizer selected from the group consisting of oligomers of lactic acid, oligomers of lactide, and mixtures thereof, wherein the oligomers have a number average molecular weight below about 5,400; and
   b. providing a second plasticizer selected from the group consisting of lactic acid, D-lactide, L-lactide, meso D,L-lactide, racemic D,L-lactide, and mixtures thereof.

10. The process of claim 4, comprising:
    a. providing a first plasticizer selected from the group consisting of one or more derivatives of an oligomer of lactic acid and an oligomer of lactide defined by the formula:

$$R'O\!\!-\!\!\left(\!\!\begin{array}{c}CH_3\\|\\C\\|\\H\end{array}\!\!-\!\!\begin{array}{c}O\\\|\\C\end{array}\!\!-\!\!O\right)_{\!\!q}\!\!R$$

where R=H, alkyl, aryl, alkylaryl or acetyl, and R is saturated, where R'=H, alkyl, aryl, alkylaryl or acetyl, and R' is saturated, where R and R' cannot both be H, and where q is an integer: $2 \leq q \leq 75$; and
    b. providing a second plasticizer selected from the group consisting of lactic acid, D-lactide, L-lactide, meso D,L-lactide, racemic D,L-lactide, and mixtures thereof.

11. The process of claim 4, in which the plasticizer is added in an amount between about 0.1 and about 10 weight percent.

12. The process of claim 4, comprising adding lactide plasticizer whereby the Tg of the material is lowered.

13. The process of claim 1, comprising the step:
    e. quenching the polymerization at a rate adapted to retain a portion of said lactide monomer as an intimately dispersed plasticizer.

* * * * *